US00RE39383E

(19) United States
(12) Reissued Patent
Liu et al.

(10) Patent Number: US RE39,383 E
(45) Date of Reissued Patent: Nov. 7, 2006

(54) PROCESS FOR 6-O-ALKYLATION OF ERYTHROMYCIN DERIVATIVES

(75) Inventors: Jih-Hua Liu, Green Oaks, IL (US); George A. Foster, Jr., Minden, NV (US); Stephen H. Montgomery, Vernon Hills, IL (US)

(73) Assignee: Abbott Laboratories, Abbott Park, IL (US)

(21) Appl. No.: 10/806,089

(22) Filed: Mar. 22, 2004

Related U.S. Patent Documents

Reissue of:
(64) Patent No.: 5,872,229
Issued: Feb. 16, 1999
Appl. No.: 08/560,752
Filed: Nov. 21, 1995

(51) Int. Cl.
*C07H 1/00* (2006.01)

(52) U.S. Cl. ..... 536/18.6; 536/7.2; 536/7.3; 536/7.4; 536/18.5

(58) Field of Classification Search ..... 536/7.2, 536/7.3, 7.4, 18.5, 18.6
See application file for complete search history.

(56) References Cited

U.S. PATENT DOCUMENTS

| | | | | |
|---|---|---|---|---|
| 3,869,444 | A | | 3/1975 | Freiberg |
| 4,331,803 | A | | 5/1982 | Watanabe et al. |
| 4,349,545 | A | | 9/1982 | Gouin d'Ambieres et al. |
| 4,476,298 | A | | 10/1984 | Morimoto et al. |
| 4,496,717 | A | | 1/1985 | Adachi et al. |
| 4,526,889 | A | | 7/1985 | Bright et al. |
| 4,640,910 | A | | 2/1987 | Faubl et al. |
| 4,668,776 | A | | 5/1987 | Yamada et al. |
| 4,670,549 | A | | 6/1987 | Morimoto et al. |
| 4,672,109 | A | * | 6/1987 | Watanabe et al. |
| 4,680,386 | A | | 7/1987 | Morimoto et al. |
| 4,740,502 | A | | 4/1988 | Hannick et al. |
| 4,833,236 | A | | 5/1989 | Morimoto et al. |
| 4,990,602 | A | * | 2/1991 | Morimoto et al. |
| 5,274,085 | A | | 12/1993 | Amano et al. |
| 5,302,705 | A | | 4/1994 | Misawa et al. |

FOREIGN PATENT DOCUMENTS

| | | | |
|---|---|---|---|
| EP | 0063489 | A1 | 10/1982 |
| EP | 0080819 | A1 | 10/1984 |
| EP | 0201166 | A1 | 11/1986 |
| EP | 0260938 | A2 | 3/1988 |
| EP | 0272110 | A2 | 6/1988 |
| EP | 0194833 | A2 | 9/1988 |

OTHER PUBLICATIONS

Judge David H. Coar, Opinion and Order on Motion for Preliminary Injunction, *Abbott Labs* v. *Teva Pharms. USA, Inc.,* Case No. 1:05CV1490 (N.D. ILL. Jun. 3, 2005).

* cited by examiner

*Primary Examiner*—Elli Peselev

(57) ABSTRACT

A procedure for preparing 6-O-alkyl erythromycin compounds having the formula:

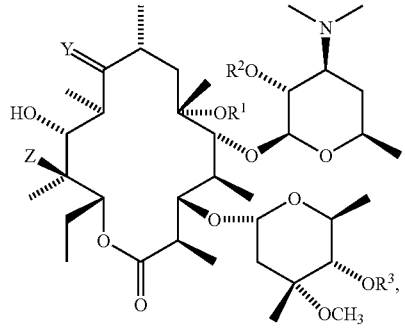

wherein $R^1$ is a loweralkyl group, $R^2$ and $R^3$ an independently hydrogen or a hydroxy-protecting group, except that $R^2$ and $R^3$ may not both be hydrogen simultaneously; Y is oxygen or a specifically substituted oxime; and Z is hydrogen, hydroxy or protected-hydroxy; by reaction of the compound wherein $R^1$ is hydrogen with an alkylating reagent, is the presence of a strong alkali metal base and also in the presence of a weak organic amino base, in a suitable stirred or agitated polar aprotic solvent, or a mixture of such polar aprotic solvents maintained at a reaction temperature and for a period of time sufficient to effect alkyation.

14 Claims, No Drawings

PROCESS FOR 6-O-ALKYLATION OF ERYTHROMYCIN DERIVATIVES

Matter enclosed in heavy brackets [ ] appears in the original patent but forms no part of this reissue specification; matter printed in italics indicates the additions made by reissue.

FIELD OF THE INVENTION

The present invention relates to a process for the preparation of 6-O-alkyl derivatives of erythromycin A and B which have use as intermediates for the synthesis of antibacterial agents. Of particular interest is use of the invention to prepare 6-O-methylerythromycin A (i.e., clarithromycin) in higher yields.

BACKGROUND

The 6-O-methylation of various erythromycin derivatives has been reported in several patents or published applications. U.S. Pat. No. 4,496,717 (issued Jan. 25, 1985) describes the methylation of a 2'-O-,1'-N-dibenzyloxycarbonyl derivative of erythromycin by reaction with a methylating reagent in the presence of a base such as in alkali metal hydride or an alkali metal amide. U.S. Pat. No. 4,670,549 (issued Jan. 2, 1997) describes the reaction of a quaternary salt of an erythromycin A 9-oxime with a methylating reagent in the presence of a bass such as an alkali metal hydride, hydroxide or alkoxide. U.S. Pat. No. 4,672,109 (issued Jun. 9,1987) describes the reaction of an erythromycin A 9-oxime with a methylating reagent in the presence of a bass such as an alkali metal hydride or hydroxide. European Application EP 260938 (published Mar. 23, 1988) describes 6-O-methylerythromycin derivatives prepared by the reaction of 2'-silylated erythromycin A 9-oximes with a methylating reagent in the presence of a base, such as an alkali, metal hydride, hydroxide or alkoxide, that is said to prevent undesirable quaternary salt formation. U.S. Pat. No. 4,990,602 (issued Feb. 5, 1991) describes additional 6-O-methylerythromcyin erythromycin A derivatives (more broadly substituted at the oxime position than those of EP 260938) prepared by the reaction of such 2'-silylated erythromycin, 9-oxime derivatives with a methylating reagent in the presence of a base such as an alkali metal hydride, hydroxide or alkoxide, also with the stated intention of preventing undesirable quaternary salt formation. While the U.S. Pat. No. 4,990,602 and the EP 260938 application point out the desirability of preventing quaternary salt formation, there remains a need for alternative methods for improving yields.

The continued appearance of new patents directed to 6-O-methyl erythromycin compounds is in indication of the importance of and the continuing efforts towards preventing unwanted side-reactions and to increasing the yield of the desired antibiotic compounds (e.g., clarithromycin).

In general, the process for making clarithromycin can be thought of as a four-step procedure beginning with erythromycin A as the starting material:

Step 1: optionally protect the 9-oxo group with an oxime;

Step 2: protect the 2'and 4"hydroxyl groups;

Step 3: methylate the 6-hydroxyl group;

Step 4: deprotect at the 2', 4'and 9-positions.

We have now found that higher yields of 6-O-alkyl erythromycin derivatives may be obtained and by-product compounds reduced by means of a 6-O-alkylation procedure that utilizes a weak organic base in the presence of a strong base. This alkyation step corresponds to the general Step 3 referred to above.

This procedure is especially useful when a mixture of hydroxy-protected erythromycin derivatives (and especially those protected with silyl compounds, e.g., trimethylsilyl) is to be methylated. Such mixtures of hydroxy-protected erythromycin derivatives (i.e., mixtures of the 2'-mono-, 4Δ-mono, and 2',4Δ-bis-protected derivatives) may be produced during large scale preparations (i.e., in Step 2 referred to above) if the bis-protection is not fully achieved. The ability to perform the alkylation on a mixture of hydroxy-protected compounds is also a distinct advantage, as costly separation steps may be avoided.

SUMMARY OF THE INVENTION

The invention comprises a procedure for preparing 6-O-alkyl erythromycin compounds having the formula (I):

(I)

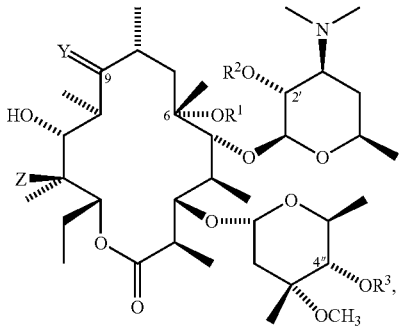

wherein:

$R^1$ is a loweralkyl group, as defined below;

$R^2$ and $R^3$ are independently hydrogen or a hydroxy-protecting group, as defined below, except that $R^2$ and $R^3$ may not both be hydrogen simultaneously;

Y is selected from the group consisting of:

a) oxygen, b) an oxime having the formula N-O-$R^4$, wherein $R^4$ is selected from the group consisting of hydrogen, a loweralkenyl group, as defined below, an aryl(loweralkyl) group, as defined below, or a substituted aryl(loweralkyl) group, as defined below; or c) an oxime having the formula

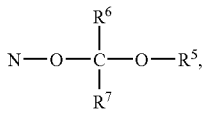

wherein $R^5$ is selected from the group consisting of:

a loweralkyl group, a cycloalkyl group, as defined below, a phenyl group, an aryl(loweralkyl) group;

or $R^5$ and $R^6$ or $R^5$ and $R^7$ and the atoms to which they are attached are taken together form a 5- to 7-membered ring containing one oxygen atom;

$R^6$ is selected from the group consisting of a loweralkyl group, a loweralkoxymethyl group, as defined below;

or $R^6$ and $R^5$ and the atoms to which they are attached are taken together from a 5- to 7-membered ring containing one oxygen atom, or $R^6$ and $R^7$ and the atoms to which they are attached are taken together form a 5- to 7-membered cycloalkyl group; and $R^7$ is selected from the group consisting of a hydrogen atom, a loweralkyl group, a phenyl group, an aryl(loweralkyl) group;

or $R^7$ and $R^5$ and the atoms to which they are attached are taken together form a 5- to 7-membered ring containing one oxygen atom;

or $R^1$ and $R^6$ and the atoms to which they are attached are taken together form a 5- to 7-membered cycloalkyl group;

with the requirement that only one pair of substituents ($R^1$ and $R^6$), ($R^5$ and $R^7$) or ($R^6$ and $R^7$) may be taken together with the atoms to which they are attached to form a ring as defined above;

and

Z is hydrogen, hydroxy or protected-hydroxy; by reaction of a compound of having the formula

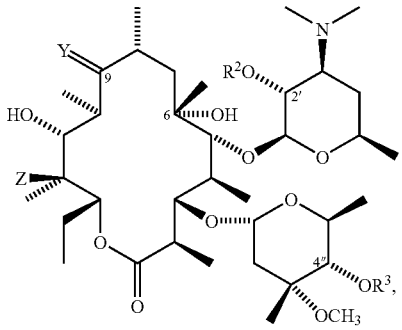

wherein $R^2$, $R^3$, Y mud Z are as defined above, with an alkylating reagent, as defined below, in the presence of a strong alkali metal base, as defined below, and also in the presence of a weak organic amino base, as defined below, in a stirred or agitated polar aprotic solvent, as defined below, or a mixture of such polar aprotic solvents maintained at a reaction temperature and for a period of time sufficient to effect alkyation.

The compounds produced by the process of the invention are subsequently deprotected at the 2' ($R^2$) and 4Δ ($R^3$) positions to give the commercially desired 60-alkyl antibacterial agents.

DETAILED DESCRIPTION OF THE INVENTION

In one embodiment (Embodiment A) of the invention is the procedure for preparing 6-O-alkyl erythromycin compounds having the formula (I):

(I)

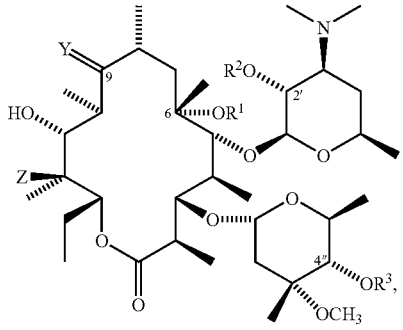

wherein:

$R^1$ is a loweralkyl group;

$R^2$ and $R^3$ are independently hydrogen or a hydroxy-protecting group, which is benzyloxycarbonyl, acetyl, or a substituted silyl group of formula $SiR^8R^9R^{10}$, wherein $R^8$, $R^9$ and $R^{10}$are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms; with the requirements that at least one of $R^8$, $R^9$ and $R^{10}$ is not a hydrogen atom and that $R^2$ and $R^3$ may not both be hydrogen simultaneously;

Y is selected from the group consisting of a) oxygen, b) an oxime having the formula N-O-$R^4$, wherein $R^4$ is selected from the group consisting of:

hydrogen, a loweralkenyl group, an aryl(loweralkyl) group, or a substituted aryl(loweralkyl) group; or c) an oxime having the formula

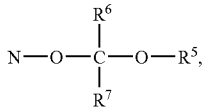

wherein $R^5$ is selected from the group consisting of:

a loweralkyl group, a cycloalkyl group, a phenyl group, an aryl(loweralkyl) group; or $R^5$ and $R^6$ or $R^5$ and $R^7$ and the atoms to which they are attached are taken together form a 5- to 7-membered ring containing one oxygen atom;

$R^6$ is selected from the group consisting of:

a loweralkyl group, a loweralkoxymethyl group;

or $R^6$ and $R^5$ and the atoms to which they are attached are taken together form a 5- to 7-membered ring containing out oxygen atom, or $R^6$ and $R^7$ and the atoms to which they are attached are taken together form a 5- to 7-membered cycloalkyl group; and $R^7$ is selected from the group consisting of:

a hydrogen atom, a lower alkyl group, a phenyl group, an aryl(loweralkyl) group, or $R^7$ and $R^5$ and the atoms to which they are attached are taken together form a 5- to 7-membered ring containing one oxygen atom;

or $R^7$ and $R^6$ and the atoms to which they are attached are taken together form a 5- to 7-membered cycloalkyl group;

with the requirement that only pair of substituents ($R^5$ and $R^6$), ($R^5$ and $R^7$ or $R^6$ and $R^7$) may be taken together with the atoms to which they are attached form to a ring as defined above;

and

Z is hydrogen, hydroxy or protected-hydroxy; by reaction of a compound having the formula:

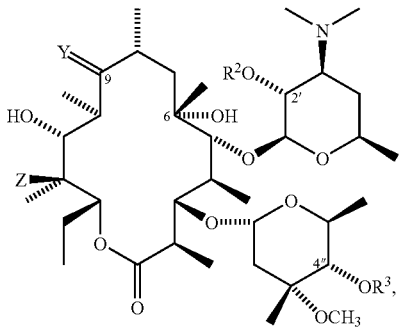

wherein $R^3$, $R^3$, Y and Z are as defined above, with an alkylating reagent, typically comprising methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate, in the presence of a strong alkali metal base, preferably selected from the group consisting of an alkali metal hydride, alkali metal hydroxide or alkali metal alkoxide, and also in the presence of a weak organic amino base, preferably selected from the group consisting of trimethylamine, triethylamine, tripropylamine, pyridine, 2-methoxypyridine, 1-methylpyrrolidine, 1-methylpiperidine, and 1-ethylpiperidine, in a suitable stirred or agitated polar aprotic solvent, selected, for example, from the group consisting of N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, or a mixture of such polar aprotic solvents maintained at a reaction temperature and for a period of time sufficient to effect alkyation, preferably from -15° C. to room temperature for a period of one to 8 hours.

In another embodiment of the invention (Embodiment B) is that procedure of Embodiment A, wherein $R^2$ and $R^3$ independently are hydrogen or a substituted silyl group of formula $SiR^8R^9R^{10}$wherein $R^8$, $R^9$ and $R^{10}$are the same or different and each is a hydrogen atom, a loweralkyl) group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms; with the requirements that at least one of $R^8$, $R^9$ and $R^{10}$ is not a hydrogen atom and that $R^2$ and $R^3$ may not both be hydrogen simultaneously.

In another embodiment of the invention (Embodiment C) is that procedure of Embodiment A, wherein Y is an oxime having the formula

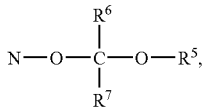

wherein $R^5$ is selected from the group consisting of:

a loweralkyl group, a cycloalkyl group, as defined below, a phenyl group, an aryl(loweralkyl) group;

or $R^5$ and $R^6$ or R-5 and $R^7$ and the atoms to which they are attached are taken together form a 5- to 7-membered ring containing one oxygen atom;

$R^6$ is selected from the group consisting of a loweralkyl group, a loweralkoxymethyl group, as defined below;

or $R^6$ and $R^5$ and the atoms to which they are attached are taken together form a 5- to 7-membered ring containing one oxygen atom, or $R^6$ and $R^7$ and the atoms to which they are attached are taken together form a 5- to 7-membered cycloalkyl group; and $R^7$ is selected from the group consisting of a hydrogen atom, a loweralkyl group, a phenyl group, an aryl(loweralkyl) group;

or $R^7$ and $R^5$ and the atoms to which they are attached are taken together form a 5- to 7-membered ring containing one oxygen atom;

or $R^7$ and $R^8$ and the atoms to which they are attached are taken together form a 5- to 7-membered cycloalkyl group;

with the requirement that only one pair of substituents ($R^5$ and $R^6$), ($R^5$ and $R^7$) or ($R^6$ and $R^7$) may be taken together with the atoms to which they are attached to form a ring as defined above;

In another embodiment of the invention (Embodiment D) is that procedure of Embodiment A, wherein Z is hydroxy.

In another embodiment of the invention (Embodiment E) is that procedure of Embodiment A, wherein the alkylating reagent is selected from the group consisting of methyl bromide, methyl iodide, dimethyl sulfate and methyl-p-toluenesulfonate.

In another embodiment of the invention (Embodiment F) is that procedure of Embodiment A, wherein the reaction is maintained at a temperature from −5° C. to +5° C.

In another embodiment of the invention (Embodiment G) is that procedure of Embodiment A, wherein the solvent is a minute of solvents consisting of N,N-dimethylformamide, dimethyl sulfoxide, N-methyl-2-pyrrolidone, hexamethylphosphoric triamide, tetrahydrofuran, 1,2-dimethoxyethane, acetonitrile and ethyl acetate, In another embodiment of the invention (Embodiment H is that procedure of Embodiment A, wherein the strong alkali metal base is an alkali metal hydroxide In another embodiment of the invention (Embodiment I) is that procedure of Embodiment A, wherein the weak organic amine base is selected from the group consisting of trimethylamine, triethylamine, tripropylamine, pyridine, 2-methoxypyridine, 1-methylpyrrolidine, 1-methylpiperidine and 1-ethylpiperidine.

In a preferred embodiment of the invention (Embodiment J) is that procedure of Embodiment A, wherein $R^2$ and $R^3$ an independently selected from hydrogen or a substituted silyl group of formula $SiR^8R^9R^{10}$, wherein $R^8$, $R^9$ and $R^{10}$are the same or different and each is a hydrogen atom, a loweralkyl group, a phenyl-substituted alkyl group in which the alkyl moiety has 1 to 3 carbon atoms, s phenyl group, a cycloalkyl group having 5 to 7 carbon atoms, or a loweralkenyl group having 2 to 5 carbon atoms and with the requirements that at least one of $R^8$ $R^9$ and $R^{10}$ is not a hydrogen atom and that both $R^2$ and $R^3$ may not be hydrogen; Y is an oxime having the formula

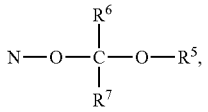

wherein $R^5$ is selected from the group consisting of
- a loweralkyl group,
- a cycloalkyl group, as defined below,
- a phenyl group.
- an aryl(loweralkyl) group;
- or $R^5$ and $R^6$ or $R^5$ and $R^7$ and the atoms to which they are attached are taken together form a 5- to 7-membered ring containing one oxygen atom;

$R^6$ is selected from the group consisting of:
- a loweralkyl group,
- a loweralkoxymethyl group, as defined below;
- or $R^6$ and $R^5$ and the atoms to which they are attached are taken together form a 5- to 7-membered ring containing one oxygen atom,
- or $R^6$ and $R^7$ and the atoms to which they are attached are taken together form a 5- to 7-membered cycloalkyl group; and $R^7$ is selected from the group consisting of:
- a hydrogen atom,
- a loweralkyl group,
- a phenyl group,
- an aryl(loweralkyl) group;
- or $R^7$ and $R^5$ and the atoms to which they are attached are taken together form a 5- to 7-membered ring containing an oxygen atom;
- or $R^7$ and R6 and the atoms to which they are attached are taken together form a 5- to 7-membered cycloalkyl group;

with the requirement that only pair of substituents ($R^5$ and $R^6$), ($R^5$ and $R^7$) or ($R^6$ and $R^7$) may be taken together with the atoms to which they are attached to form a ring as defined above;

Z is hydroxy; the alkylating reagent is a methylating reagent consisting of methyl bromide, methyl iodide, dimethyl sulfate or methyl-p-toluenesulfonate; the strong alkali metal base is an alkali metal hydroxide; wherein the weak organic amino base is selected from the group consisting of trimethylamine, triethylamine, tripropylamine, pyridine, 2-methoxypyridine, 1-methylpyrrolidine, 1-methylpiperidine, and 1-ethylpiperidine; the solvent is a mixture of solvents consisting of N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate; and the reaction is maintained at a temperature from −5° C. to 5° C.

In a more preferred embodiment of the invention (Embodiment K) is that procedure of Embodiment A, wherein $R^2$ and $R^3$ are independently hydrogen or a trimethylsilyl group but $R^2$ and $R^3$ may not both be hydrogen simultaneously; Y is a isopropyl cyclohexyl ketal oxime group; Z is hydroxy; the alkylating reagent consists of methyl bromide, methyl iodide, dimethyl sulfate, or methyl-p-toluenesulfonate; the strong alkali metal base is potassium hydroxide; the weak organic amine base is triethylamine; the solvent is a mixture of THF and DMSO; and the reaction is maintained at a temperature from −5° C. to 0° C.

In another aspect of the invention are the novel intermediate compounds, 4"-TMS-erythromycin A oxime IPCH ketal and 2'-TMS-erythromycin A oxime IPCH ketal.

DEFINITIONS

A number of defined terms are used herein to designate particular elements of the present invention. When so used, the following meanings an intended:

The term "alkyl" refers to saturated, straight- or branched-chain hydrocarbon radicals containing between one and ten carbon atoms including, but not limited to, methyl, ethyl, propyl, isopropyl, n-butyl, tert-butyl and neopentyl.

The term "alkylating reagent" refers to a reagent capable of placing an alkyl group onto a nucleophilic site, including, but not limited to, alkyl halides such as methyl bromide, ethyl bromide, n-propyl bromide, methyl iodide, ethyl iodide, n-propyl bromide; dialkyl sulfates such as dimethyl sulfate, diethyl sulfate, di-n-propyl sulfate; and alkyl or aryl sulfonates such as methyl-p-toluenesulfonate, ethyl methanesulfonate, n-propyl methanesulfonate, and the like.

The term "aryl(loweralkyl)" refers to a loweralkyl radical having appended thereto 1–3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among loweralkyl, halo(loweralkyl), loweralkoxy, halogen. Examples of cycloalkyl radicals include, but are not limited to, cyclopropyl, cyclobutyl, cyclopentyl, cyclohexyl, cycloheptyl, 1-fluoro-cyclopropyl, 2-fluorocyclopropyl and 2-aminocyclopropyl.

The term "hydroxy-protecting group" is well-known in the art and refers to substituents on functional hydroxy groups of compounds undergoing chemical transformation which prevent undesired reactions and degradations during a synthesis (see, for example, T. H. Greene and P. G. M. Wuts, Protective Groups in Organic Synthesis, 2nd edition, John Wiley & Sons, New York (1991)). Examples of hydroxy-protecting groups include, but are not limited to, benzyloxycarbonyl, acetyl, or a substituted silyl group of formula $SiR^8R^9R^{10}$, wherein $R^8$, $R^9$ and $R^{10}$ are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms and wherein at heat one of $R^8$, $R^9$ and $R^{10}$ is not a hydrogen atom; and the like The term "loweralkenyl" refers to a straight-or branched-chain hydrocarbon radical containing between two and six carbon atoms and possessing at least are carbon-carbon double bond. Examples of loweralkenyl radicals include vinyl, allyl, 2- or 3-butenyl, 2-,3- or 4-pentenyl, 2-,3-,4- or 5-hexenyl and isomeric forms thereof.

The term "loweralkoxy" refers to an loweralkyl radical which is joined to the rest of the molecule via an ether linkage (i.e., through in oxygen atom). Examples of loweralkoxy radicals include, but are not limited to, methoxy and ethyloxy.

The term "loweralkyl" refers to an alkyl radical containing one to six carbon atoms including, but not limited to, methyl, ethyl, propyl, isopropyl, n-butyl, tert-butyl and neopentyl.

The term "protected hydroxy" refers to a hydroxy group protected with a hydroxy protecting group, as defined above.

The term "polar aprotic solvent" refers to polar organic solvents lacking an easily removed proton , including, but not limited to N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, and the like.

The term "strong alkai metal base" refers to an alkali metal horse having a weak conjugate acid, including, but not limited to, sodium hydroxide, postassium hydroxide, sodium hydride, potassium hydride, potassium t-butoxide, and the like.

The term "substituted aryl(loweralkyl)" refers to an aryl (loweralkyl) residue as defined above having between one and that non-hydrogen ring substituents each independently selected from among halogen, loweralkoxy, loweralkyl, hydroxy-substituted loweralkyl, and (loweralkyl)amino. Examples of substituted aryl (loweralkyl) radicals include 2-fluorophenylmethyl, 4-fluorophenylethyl and 2,4-difluorophenylpropyl The term "weak organic amine base" refers to as organic amine base having a strong conjugate acid, including, but not limited to trimethylamine, triethylamine, tripropylamine, pyridine, 2-methoxypyridine, 1-methylpyrrolidine, 1-methylpiperidine, and 1-ethylpiperidine, and the like.

ABBREVIATIONS

Certain abbreviations are used repeatedly in the specification which follows. These include: DMSO for dimethyl sulfoxide; HPLC for high performance liquid chromatography; IPCH ketal for isopropyl cyclohexyl ketal; TEA for triethylamine; THF for tetrahydrofuran; TMS for trimethylsilyl.

STARTING MATERIALS

2',4"-bisTMS-erythromycin A oxime IPCH ketal was prepared as described in Example 30 of U.S. Pat. No. 4,990,602.

Preparation of 4"-TMS-erythromycin A oxime IPCH ketal

4"-TMS-erythromycin A oxime IPCH ketal was prepared by treating 2',4"-bisTMS-erythromycin A oxime IPCH ketal with acetic acid in a mixture of THF, DMSO and isopropyl alcohol at room temperature for 2 hours and 20 minutes, then diluting the mixture with isopropyl acetate and quenching with excess 2N NaOH. The organic layer was separated and dried, and the solvent was removed under vacuum to afford the 4"-TMS-erythromycin A oxime IPCH ketal. $^1$H NMR assignments for the desosamine portion of the molecule are: 1', 4.57; 2', 3.20; 3', 2.44, 4', 1.69 & 1.21; 5', 3.45; 6', 1.21; OTMS (9H), 0.12. The integral of the TMS signal (9H) indicates that a single TMS group is present in the molecule. An NOE in the ROESY spectrum between the TMS group at 0.12 ppm and H2'at 3.20 ppm indicates that the TNS group is at the 2'position.

2'-TMS-erythromycin A oxime IPCH ketal 2'-TMS-erythromycin A oxime IPCH ketal was prepared by treating 2',4"-bisTMS-erythromycin A oxime IPCH ketal with 0.5N NaOH and TEA in 1:1 THF:DMSO for 2.5 hours at room temperature. The reaction was quenched with heptane and 2N NaOH, and the layers were separated. The organic layer was washed with water and dried over MgSO4, then the solvent was removed under vacuum with additional flushing of the heptane with nitrogen to afford the 2'-TMS-erythromycin A oxime IPCH ketal. The structure was confirmed by NMR. $^1$H NMR assignments for the cladinose portion of the molecule are: 1", 4.90; 2", 2.36 & 1.50; 3"-methyl, 1.14; 4", 3.16; 5", 4.24; 6", 1.22; Omethyl, 3.29; OTMS (9H), 0.14. The integral of the TMS signal (9H) indicates that a single TMS group is present in the molecule. An NOE in the ROESY spectrum between the TMS group at 0.14 ppm and H4"at 3.16 ppm indicates that the TMS group is at the 4"position.

EXAMPLES

The following examples, which are provided for illustration and not limitation of the invention, will save to further illustrate the process and the advantages of the invention.

Where mixtures of starting material are utilized, the starting material is dissolved in the appropriate solvent and analyzed by HPLC, thus providing an exact estimate of each individual compound. A similar HPLC analysis was performed on the mixtures of products, to provide an exact estimate of each product compound.

Example 1

Methylation of 2', 4"-bisTMS-erythromycin A oxime IPCH ketal:

Reference methylation procedure with KOH base and no TEA

A solution of 2', 4"-bisTMS-erythromycin A oxime IPCH ketal (4.0 mmol) in 1:1 THF:DMSO (50 mL) was prepared. The solution was cooled to 0°–5° C., and methyl iodide (2.34 g, 16.5 mmol) and KOH (0:47 g. 8.3 mmol) were added in that order. The reaction mixture was stirred for 60 minutes, the reaction was diluted by addition of 100 mL of heptane, and 20 mL of 2N NaOH were added to quench the reaction. The layers were separated, and the organic layer was washed with water. The heptane layer was dried over MgSO4, and the solvent was removed under vacuum to afford 3.86 g of product containing 2.99 g of the 6-O-methyl-2',4"-bisTMS-erythromycin A oxime IPCH ketal (71% yield). The identity of the product was confirmed by HPLC analysis and comparison with the reference product (see U.S. Pat. No. 4,990,602). See Table 1 below for a summary of Examples 1, 2 and 3.

Example 2

Methylation of 2',4"-bisTMS-erythromycin A oxime IPCH ketal;

Methylation Procedure with KOH and Low Level of TEA

The procedure of Example 1 was was followed, except TEA (1.0 g, 10 mmole) was added prior to the addition of the methyl iodide and KOH. A crude product (4.14 g) was obtained which contained 3.4 g of the 6-O-methyl products (81% yield). See Table 1 below for a summary of Examples 1,2 and 3.

Example 3

Methylation of 2', 4"-bisTMS-erythromycin A oxime IPCH ketal;

Methylation procedure with KOH and high level of TEA

The procedure of Example 1 was was followed, except TEA (3.5 g, 34.6 mmole) was added prior to the addition of the methyl iodide and KOH. A crude product (3.84 g) was obtained which contained 3.5 g of the 6-O-methyl products (83%). See Table 1 below for a summary of Examples 1, 2 and 3.

TABLE 1

Summary of Examples 1, 2 and 3.

| Ex. No. | Base | starting material (mmol) | 6-O-methyl prod (g) | yield (%) |
|---|---|---|---|---|
| 1 | KOH | 4.0 | 2.99 | 71 |
| 2 | KOH + low TEA | 4.0 | 3.4 | 81 |
| 3 | KOH + high TEA | 4.0 | 3.5 | 83 |

These data demonstrate that higher yields of product are obtained in the presence of TEA and that the yield is highest at the higher TEA level.

Example 4

Methylation of a mixture of 2',4"-bisTMS-erythromycin A oxime IPCH ketal and 4"-TMS erythromycin A oxime IPCH ketal;

Reference methylation procedure with KOH base and no TEA

A solution of a mixture of 2',4"-bisTMS-erythromycin A oxime IPCH ketal and 4"-TMS-erythromycin A oxime IPCH ketal (3.07 and 1.0 mmol, respectively) in 1:1 THF:DMSO (50 mL) was prepared. The solution was cooled to 0°5° C., and methyl bromide (0.85 g, 9.0 mmol) and KOH (0.47 g, 8.3 mmol) were added in that order. The reaction mixture was stirred for 30 minutes, then the reaction was diluted by addition of 100 mL of heptane, and 20 mL of 2N NaOH were added to quench the reaction. The layers were separated, and the organic layer was washed with water. The layers were separated, and a gummy by-product was collected. The heptane layer was dried over MgSO4, and the solvent was removed under vacuum to afford 2.95 g of product identified as the 6-O-methyl-2',4"-bisTMS-erythromycin A oxime IPCH ketal (overall yield 69%). No methylated 4"-TMS product was obtained. The identity of the product was confirmed by comparison of its NMR spectrum with that of the reference product (see U.S. Pat. No. 4,990,602). The gummy by-product was dissolved in 25 mL of isopropyl acetate. The solution was dried and filtered, and the solvent removed under vacuum to give 0.91 g of a material identified as a quaternary salt by NMR spectroscopy. See Table 2 below for a summary of Examples 4, 5 and 6.

Example 5

Methylation of a mixture of 2',4"-bisTMS-erythromycin A oxime IPCH ketal and 4"-TMS-erythromycin A oxime IPCH ketal:

Methylation procedure with KOH and low level of TEA

The procedure of Example 4 was followed, except that the order of addition of reagents to the solution of starting materials was TEA (1.0 g, 10.0 mmol), methyl bromide, then KOH, to afford 3.93 g of a mixture of desired products, 6-O-methyl-2',4"-TMS-erythromycin A oxime IPCH ketal and 6-O-methyl-4"-TMS-erythromycin A oxime IPCH ketal (2.58 and 0.44 mmol, respectively; overall yield 74%). A modest amount of the quaternary by-product (0.41 g) was isolated. See Table 2 below for a summary of Examples 4, 5 and 6.

Example 6

Methylation of a mixture of 2',4"-bisTMS-erythromycin A oxime IPCH ketal and 4"-TMS-erythromycin A oxime IPCH ketal;

Methylation procedure with KOH and high level of TEA

The procedure of Example 4 was followed, except that the order of addition of reagents to the solution of starting materials was TEA (3.5 g, 34.6 mmol), methyl bromide, then KOH, to afford 3.87 g of a mixture of desired products, 6-O-methyl-2',4"-bisTMS-erythromycin A oxime IPCH ketal and 6-O-methyl-bisTMS-erythromycin A oxime IPCH ketal (2.48 and 0.72 mmol, respectively; overall yield 79%). A trace amount of the quaternary by-product was obtained. See Table 2 below for a summary of Examples 4, 5 and 6

TABLE 2

Summary of Example 4, 5 and 6.

| Ex. No. | Base | starting material (mmol) 2',4'-bis-TMS | starting material (mmol) 4'-mono-TMS | 6-O-methyl product (mmol) 2',4'-bis-TMS | 6-O-methyl product (mmol) 4'-mono-TMS | combined yield % |
|---|---|---|---|---|---|---|
| 4 | KOH | 3.07 | 1.0 | 2.81 | 0 | 69 |
| 5 | KOH + low TEA | 3.07 | 1.0 | 2.58 | 0.45 | 74 |
| 6 | KOH + high TEA | 3.07 | 1.0 | 2.48 | 0.72 | 79 |

These data demonstrate that higher combined yields of product are obtained in the presence of TEA and that combined yields are highest at the higher TEA level.

Example 7

Methylation of mono-protected 4"-TMS-erythromycin A oxime IPCH ketal:

Methylation procedure with KOH only:

4"-TMS-erythromycin A oxime IPCH ketal (2.1 g 2.2 mmol) was dissolved in 1:1 THF:DMSO (25 mL). The solution was cooled to 0°–5° C., and methyl bromide (1.5 mL, 27 mmol) and KOH (0.2 g, 3.0 mmol) were added in that order. The reaction mixture was stirred for 1 hour, the reaction was diluted by addition of 50 mL of heptane, and 10 mL of 2N NaOH were added to quench the reaction. The layers were separated, a gummy by-product was collected, and the organic layer was washed with water. The heptane layer was dried over MgSO4, and the solvent was removed under vacuum. No product was observed. The gummy by-product was dissolved in 50 mL of isopropyl acetate. The solution was dried and filtered, and the solvent was removed under vacuum to give 1.5 g of a material identified as a quaternary ash by NMR spectroscopy. See Table 3 below for a summary of Examples 7 and 8.

Example 8

Methylation of mono-protected 4"-TMS-erythromycin A oxime IPCH ketal;

Methylation procedure with KOH and TEA:

The procedure of Example 7 was followed, except that the order of addition of reagents to the solution of starting material was TEA (3.5 g. 34.6 mmol), methyl bromide (0.5 mL, 9 mmol), then KOH (0.26 g, 3.9 mmol), to afford 1.32 g of the desired product, 6-O-methyl-4"-TMS-erythromycin A oxime IPCH keel (68% yield), and 0.32 g of the quaternary by-product. See Table 3 below for a summary of Examples 7 and 8.

TABLE 3

Summary of Examples 7 and 8.

| Ex. No. | Base | starting material (mmol) | 6-O-methyl prod (g) | yield (%) |
|---|---|---|---|---|
| 7 | KOH | 2.2 | 0 | 0 |
| 8 | KOH + high TEA | 2.2 | 1.32 | 68 |

These data demonstrate 80 yield of 4'-mono-protected product is obtained without the presence of TEA.

Example 9

Methylation of mono-protected 2'-TMS-erythromycin A oxime IPCH ketal:

Methylation procedure with KOH only

2'-TMS-erythromycin A oxime IPCH ketal (2.1 g, 2.2 mmol) was dissolved in 1:1 THF:DMSO (25 mL). The solution was cooled to 0°–5° C., and methyl bromide (1.0 mL 2.8 mmol) and KOH (0.2 g, 3.0 mmol) were added in that order. The reaction mixture was stirred for 1 hour, the reaction was diluted by addition of 50 mL of heptane, and 10 mL of 2N NaOH were added to quench the reaction. The layers were separated, a gummy by-product was collected, and the organic layer was washed with water. The heptane layer was dried over MgSO4, and the solvent was removed under vacuum to afford 1.54 g of 6-O-methyl-2'-TMS-erythromycin A oxime IPCH ketal (69% yield). The gummy by-product was dissolved in 50 mL of isopropyl acetate. The solution was dried and filtered, and the solvent was removed under vacuum to give 0.36 g of a material identified as a quaternary salt by NMR spectroscopy. See Table 4 below for a summary of Examples 9 and 10.

Example 10

Methylation of mono-protected 2'-TMS-erythromycin A oxime IPCH ketal:

Methylation procedure with KOH and TEA

The procedure of Example 9 was followed, except that the order of addition of reagents to the solution of starting material was TEA (1.75 g, 17.3 mmol), methyl bromide (0.5 mL, 9.0 mmol), then KOH (0.23 g, 3.0 mmol), to afford 1.84 g of the desired product, 6-O-methyl-2'-TMS-erythromycin A oxime IPCH ketal (74.5% yield), and 0.1 g of the quaternary by-product. See Table 4 below for a summary of Examples 9 and 10.

TABLE 4

Summary of Examples 9 and 10.

| Ex. No. | Base | starting material (mmol) | 6-O-methyl prod (g) | yield (%) |
|---|---|---|---|---|
| 9 | KOH | 2.2 | 1.54 | 69 |
| 10 | KOH + TEA | 2.2 | 1.84 | 74.5 |

These data demonstrate that higher yields of 2'-mono-protected product is obtained in the presence of TEA.

We claim:

1. An improved process for selective alkylation of a hydroxy group at the 6-position of a compound of the formula:

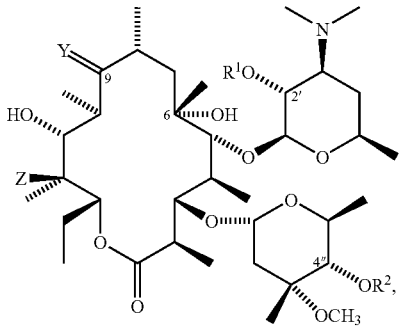

wherein:

$R^1$ and $R^2$ are independently hydrogen or a hydroxy-protecting group, except that $R^1$ and $R^2$ may not both be hydrogen simultaneously;

Y is selected from the group consisting of a) oxygen, b) an oxime having the formula N-O-$R^3$, wherein $R^3$ is selected from the group consisting of hydrogen, a loweralkenyl group, an aryl(loweralkyl) group, or a substituted aryl(loweralkyl) group; and c) to oxime having the formula:

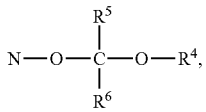

wherein $R^4$ is a loweralkyl group, a cycloalkyl group;

a phenyl group, an aryl(loweralkyl) group;

or $R^4$ and $R^5$ or $R^4$ and $R^6$ and the atoms to which they and attached are taken together form a 5- to 7-membered ring containing one oxygen atom;

$R^5$ is a loweralkyl group;

a loweralkoxymethyl group;

or $R^5$ and $R^4$ and the atoms to which they are attached are taken together form a 5- to 7-membered ring containing one oxygen atom, or $R^5$ and $R^6$ and the atoms to which they are attached are taken together form a 5- to 7-membered cycloalkyl group; and $R^6$ is a hydrogen atom, a loweralkyl group, a phenyl group, an aryl(loweralkyl) group;

or $R^6$ and $R^4$ and the atoms to which they are attached are taken together form a 5- to 7-membered ring containing one oxygen atom;

or $R^6$ and $R^5$ and the atoms to which they are attached are taken together form a 5- to 7-membered cycloalkyl group;

with the requirement that only one pair of substituents ($R^4$ and $R^5$), ($R^4$ and $R^6$) or ($R^5$ and $R^6$) may be taken together with the atoms to which they are attached to form a ring as defined above; and Z is hydrogen, hydroxy or protected-hydroxy;

comprising reacting the compound with an alkylating agent in the presence of both a strong alkali metal base and a weak organic amine base in polar aprotic solvent or a mixture of polar aprotic solvents maintained at a reaction temperature for a period of time sufficient to complete the alkylation, by adding the weak organic base prior to the addition of the alkylating agent and the strong alkali metal base.

2. The process according to claim 1, wherein the weak organic amine base is selected from the group consisting of trimethyl-amine, triethylamine, tripropylamine, pyridine, 2-methoxypyridine, 1-methyl-pyrrolidine, 1-methylpiperidine, and 1-ethylpiperidine.

3. The process according to claim 1, wherein the alkylating agent is selected from the group consisting of methyl bromide, methyl iodide, dimethyl sulfate and methyl-p-toluenesulfonate.

4. The process according to claim 1, wherein the solvent is a mixture of solvents selected from the group consisting of N,N-dimethyl-formamide, dimethyl sulfoxide, N-methyl-2-pyrrolidone, hexamethylphosphoric triamide, tetrahydrofuran, 1,2-dimethoxyethane, acetonitrile and ethyl acetate.

5. The process according to claim 1, wherein $R^1$ and $R^2$ in the compound are independently hydrogen or a hydroxy-protecting group, which is benzyloxycarbonyl, acetyl, or a substituted silyl group of formula $SiR^7R^8R^9$, wherein $R^7$, $R^8$ and a $R^9$ are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms; with the provisions that at least one of $R^7$, $R^8$ and $R^9$ is not a hydrogen atom.

6. The process according to claim 1, wherein the compound is 2'mono trimethylsilyl erythromycin A oxime isopropyl cyclohexyl ketal, or 4" monotrimethylsilyl erythromycin A oxime isopropyl cyclohexyl ketal.

7. The process according to claim 1, wherein the compound is a mixture of 2' mono trimethylsilyl erythromycin A oxime isopropyl cyclohexyl ketal and 4" monotrimethylsilyl erythromycin A oxime isopropyl cyclohexyl ketal.

*8. An improved process for preparing 6-O-methylerythromycin A comprising;*

*(a) reacting a compound of the formula*

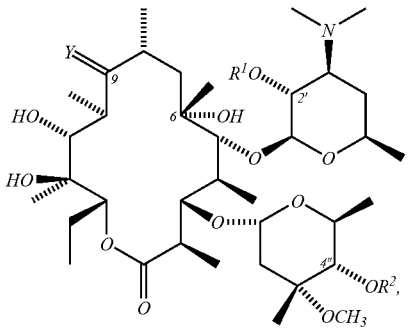

*wherein:*

*$R^1$ and $R^2$ are independently hydrogen or a hydroxy-protecting group, except that $R^1$ and $R^2$ may not both be hydrogen simultaneously; and*

*Y is selected from the group consisting of:*

*a) oxygen,*

*b) an oxime having the formula N-O-$R^3$, wherein $R^3$ is selected from the group consisting of:*

*hydrogen,*

*a loweralkenyl group,*

*an aryl(loweralkyl) group, or*

*a substituted aryl(loweralkyl) group; and*

*c) an oxime having the formula:*

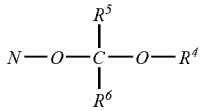

*wherein*

*$R^4$ is*

*a loweralkyl group,*

*a cycloalkyl group,*

*a phenyl group,*

*an aryl(loweralkyl) group,*

*or $R^4$ and $R^5$ or $R^4$ and $R^6$ and the atoms to which they are attached are taken together form a 5- to 7-membered ring containing one oxygen atom;*

*$R^5$ is*

*a loweralkyl group,*

*a loweralkoxymethyl group,*

*or $R^5$ and $R^4$ and the atoms to which they are attached are taken together form a 5- to 7-membered ring containing one oxygen atom,*

*or $R^5$ and $R^6$ and the atoms to which they are attached are taken together form a 5- to 7-membered cycloalkyl group; and*

*$R^6$ is*

*a hydrogen atom,*

*a loweralkyl group,*

*a phenyl group,*

*an aryl(loweralkyl) group;*

*or $R^6$ and $R^4$ and the atoms to which they are attached are taken together form a 5- to 7-membered ring containing one oxygen atom,*

*or $R^6$ and $R^5$ and the atoms to which they are attached are taken together form a 5- to 7-membered cycloalkyl group;*

*with the requirement that only one pair of substituents ($R^4$ and $R^5$), ($R^4$ and $R^6$) or ($R^5$ and $R^6$) may be taken together with the atoms to which they are attached to form a ring as defined above;*

*with a methylating agent in the presence of both a strong alkali metal base and a weak organic amine base in polar aprotic solvent or a mixture of polar aprotic solvents maintained at a reaction temperature for a period of time sufficient to complete the methylation, by adding the weak organic base prior to the addition of the methylating agent and the strong alkali metal base; and*

*(b) deprotecting at the 2' and/or 4" positions, and optionally deprotecting at the 9 position.*

*9. The process according to claim 8, wherein the weak organic amine base is selected from the group consisting of trimethylamine, triethylamine, tripropylamine, pyridine, 2-methoxypyridine, 1-methyl-pyrrolidine, 1-methylpiperidine, and 1-ethylpiperidine.*

*10. The process according to claim 8, wherein the methylating agent is selected from the group consisting of methyl bromide, methyl iodide, dimethyl sulfate and methyl-p-toluenesulfonate.*

*11. The process according to claim 8, wherein the solvent is a mixture of solvents selected from the group consisting of N,N-dimethyl-formamide, dimethyl sulfoxide, N-methyl-2-pyrrolidone, hexamethylphosphoric triamide, tetrahydrofuran, 1,2-dimethoxyethane, acetonitrile and ethyl acetate.*

*12. The process according to claim 8, wherein $R^1$ and $R^2$ in the compound are independently hydrogen or a hydroxy-protecting-group, which is benzyloxycarbonyl, acetyl, or a substituted silyl group of formula $SiR^7R^8R^9$, wherein $R^7$, $R^8$ and $R^9$ are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms; with the provision that at least one of $R^7$, $R^8$ and $R^9$ is not a hydrogen atom.*

*13. The process according, to claim 8, wherein the compound is 2' mono trimethylsilyl erythromycin A oxime isopropyl cyclohexyl ketal, or 4"monotrimethylsilyl erythromycin A oxime isopropyl cyclohexyl ketal.*

*14. The process according to claim 8, wherein the compound is a mixture of 2" mono trimethylsilyl erythromycin A oxime isopropyl cyclohexyl ketal and 4" monotrimethylsilyl erythromycin A oxime isopropyl cyclohexyl ketal.*

* * * * *

UNITED STATES PATENT AND TRADEMARK OFFICE

CERTIFICATE OF CORRECTION

PATENT NO. : RE 39,383 E
APPLICATION NO. : 10/806089
DATED : November 7, 2006
INVENTOR(S) : Jih-Hua Liu et al.

It is certified that error appears in the above-identified patent and that said Letters Patent is hereby corrected as shown below:

Title page, item [57] Abstract line 13: "sufficient to effect alkyation." to read as --sufficient to effect alkylation.--

Column 1, line 63, "sufficient to effect alkyation." to read as --sufficient to effect alkylation.--

Column 3, line 51, "sufficient to effect alkyation" to read as --sufficient to effect alkylation--

Column 4, line 61, "containing out oxygen atom" to read as --containing one oxygen atom--

Column 5, line 11, "attached form to a ring" to read as --attached to form a ring--

Column 5, line 51, "sufficient to effect alkyation." to read as --sufficient to effect alkylation.--

Column 7, line 5, "s phenyl group" to read as --a phenyl group--

Column 8, line 41, "halo(loweralkyl), loweralkoxy, halogen." to read as --halo(loweralkyl), loweralkoxy and halogen.--

Column 8, line 60, "and wherein at heat one of" to read as --and wherein at least one of--

Column 9, line 13, "an easily removed proton ," to read as --an easily removed proton,--

Column 9, line 18, "The term "strong alkai metal base"" to read as --The term "strong alkali metal base"--

Column 9, line 20, "postassium hydroxide" to read as --potassium hydroxide--

Column 10, line 52, "Example 1 was was followed" to read as --Example 1 was followed--

Column 10, line 62, "Example 1 was was followed" to read as --Example 1 was followed--

Signed and Sealed this

Twelfth Day of October, 2010

David J. Kappos

David J. Kappos
*Director of the United States Patent and Trademark Office*